(12) United States Patent
Gross et al.

(10) Patent No.: US 6,174,908 B1
(45) Date of Patent: Jan. 16, 2001

(54) POTASSIUM CHANNEL INHIBITORS

(75) Inventors: Michael F. Gross, Durham, NC (US); Neil A. Castle, Huntingdon (GB); Jose S. Mendoza, Durham, NC (US)

(73) Assignees: ICAGen, Inc., Durham, NC (US); Eli Lilly & Company Lilly Corporate Center, Indianapolis, IN (US)

( * ) Notice: Under 35 U.S.C. 154(b), the term of this patent shall be extended for 0 days.

(21) Appl. No.: 09/307,708

(22) Filed: May 1, 1999

Related U.S. Application Data

(60) Provisional application No. 60/088,228, filed on Jun. 5, 1998.

(51) Int. Cl.[7] .................... A61K 31/425; C07D 277/02
(52) U.S. Cl. .................... 514/369; 548/182; 548/184; 548/186; 548/189
(58) Field of Search .................... 548/182, 184, 548/186, 187, 188, 189; 514/369

(56) References Cited

U.S. PATENT DOCUMENTS

| | | | |
|---|---|---|---|
| 4,053,471 | 10/1977 | Krapcho | 544/133 |
| 4,436,739 | * 3/1984 | Krumkalus | 424/246 |
| 4,535,164 | 8/1985 | Pardo et al. | 548/187 |
| 5,061,720 | 10/1991 | Walsh et al. | 514/369 |
| 5,549,974 | 8/1996 | Holmes | 428/403 |

FOREIGN PATENT DOCUMENTS

| | | |
|---|---|---|
| 2259 222 | 6/1973 | (DE) . |
| 0 010 420 A1 | 4/1980 | (EP) . |
| 0 292 305 A1 | 11/1988 | (EP) . |
| 0 705 816 A1 | 4/1996 | (EP) . |
| 0 799 614 A1 | 10/1997 | (EP) . |
| 1409898 | 10/1995 | (GB) . |
| 57-099523 | 6/1982 | (JP) . |
| WO 96/20936 | 7/1996 | (WO) . |

OTHER PUBLICATIONS

Surrey, Alexander, "The Preparation of 4–Thiazolidones by the Reaction of Thioglycolic Acid with Schiff Bases", JACS, Nov, 1947, vol. 69, pp. 2911–2913.
Surrey, Alexander, "The Preparation of 2,3–Disubstituted–4–thiazolidones", JACS, Dec. 1948, vol. 70, pp. 4262–4263.
Aukt–Justus, et al., "Generation of a Library of 4–Thiazolidnones Utilizing Polymer Supported Quench (PSQ) Reagent Methodology", Biotechnology and Bioengineering (Combinatorial Chemistry), 61(1) Winter 1996, pp. 17–22.
ACS Computer Database Search Results pp. 1–127.
Beilstein Computer Database Search Results pp. 1–7.
Derwent Computer Database Search Results pp. 1–6.
Misc. Computer Database Search Results (WPAT) 1–183.
P. Singh et al., *Indian Journal of Pharmaceutical Sciences*, vol. 57, No. 4, 1995, pp. 162–165, XP–002118096, p. 163.
T. Koga et al., *British Journal of Pharmacology*, vol. 123, No. 7, Apr. 1998 (1998–04), pp. 1409–1417, XP002118097, p. 1409, abstract; p. 1410, compound CP–060S.
Y. Ohya et al., *European Journal of Pharmacology*, vol. 330, No. 1, 1997, pp. 93–99, XP002118098, p. 93, abstract; p. 93, paragraph 1 ("Introduction"); pp. 96, 97, paragraph 3.2.

* cited by examiner

*Primary Examiner*—Mukund J. Shah
*Assistant Examiner*—Sudhaker B. Patel
(74) *Attorney, Agent, or Firm*—Banner & Witcoff, Ltd.

(57) ABSTRACT

Certain thiazolidinone and metathiazanone compounds, as described, are useful as potassium channel inhibitors and are especially useful for the treatment of cardiac arrhythmias and other diseases, conditions and disorders.

7 Claims, No Drawings

POTASSIUM CHANNEL INHIBITORS

This application claims the benefit under 35 U.S.C. 119 (e)(1) of prior filed provisional application 60/088,228 filed Jun. 5, 1998.

BACKGROUND OF THE INVENTION

1. Field of the Invention

The present invention is broadly directed to a class of thiazolidinone and metathiazanone compounds and their derivatives useful as potassium channel inhibitors.

2. Description of Related Art

Potassium channels are expressed in eukaryotic and procaryotic cells, and are elements in the control of electrical and nonelectrical cellular functions. Subclasses of these channels have been named based on amino acid sequence and functional properties, and include for example voltage gated potassium channels (e.g., Kv1, Kv2, Kv3, Kv4). Subtypes within these subclasses have been characterized as to their putative function, pharmacology and distribution in cells and tissues (Chandy and Gutman, "Voltage-gated potassium channel genes" in Handbook of Receptors and Channels-Ligand and Voltage-gated Ion Channels, ed. R. A. North, 1995; Doupnik et al., *Curr. Opin. Neurobio.* 5:268, 1995).

Inhibitors of potassium channels lead to a decrease in potassium ion movement across cell membranes. Consequently, such inhibitors induce prolongation of the electrical action potential or membrane potential depolarization in cells containing the inhibited or blocked potassium channels. Prolonging of the electrical action potential is a preferred mechanism for treating certain diseases, e.g., cardiac arrhythmias (Colatsky et al., *Circulation* 82:2235, 1990). Membrane potential depolarization is a preferred mechanism for the treating of certain other diseases, such as those involving the immune system (Kaczorowski and Koo, *Perspectives in Drug Discovery and Design*, 2:233, 1994).

Potassium channels which exhibit functional, pharmacological and tissue distribution characteristics have been cloned. These cloned potassium channels are useful targets in assays for identifying candidate compounds for the treatment of various disease states. For example, the delayed rectifier voltage-gated potassium channel termed $I_{kur}$ or $I_{SUS}$ which has been reported to contain the Kv1.5 α-subunit gene product is generally believed to be important in the repolarization of the human atrial action potential and thus is a candidate potassium channel target for the treatment of cardiac arrhythmias especially those occurring in the atria (Wang et al., *Circ. Res.* 73:1061, 1993; Fedida et al., *Circ. Res.* 73:210, 1993; Wang et al., *J Pharmacol. Exp. Ther.* 272:184, 1995; Amos et al., *J Physiol.*, 491:31, 1996).

The present invention is related to thiazolidinone and metathiazanone compounds which have been found to be useful as inhibitors of potassium channel function. Such compounds have been found to be especially active as inhibitors of voltage-gated potassium channels and may therefore be utilized for the treatment of diseases, conditions and disorders in which prolongation of cellular action potentials or the induction of cell membrane depolarization would be beneficial. These disease states, conditions and disorders include, but are not limited to cardiac arrhythmias, cell proliferative disorders including cancer, disorders of the auditory system, central nervous system mediated motor dysfunction and disorders of pulmonary, vascular and visceral smooth muscle contractility.

It is an object of the present invention, therefore, to provide a method of treating diseases, conditions and disorders in mammals, including humans, which respond to the inhibition of potassium channel function, which method comprises administering to a mammal in need thereof certain thiazolidinone or metathiazanone compounds.

Another object of the invention is to provide certain thiazolidinone and metathiazanone compounds which are useful for the treatment of such diseases, conditions and disorders in mammals, including humans.

DETAILED DESCRIPTION OF THE INVENTION

This invention describes certain thiazolidinone and metathiazanone compounds and their utility as inhibitors of voltage-dependent potassium channel function, particularly potassium channels (i.e., $I_{Kur}$, Kv1.5) that could serve as targets for the treatment of cardiac arrhythmias especially those occurring in the atria (e.g., atrial flutter and atrial fibrillation) (Wang et al., *Circ. Res.* 73:1061, 1993; Fedida et al., *Circ. Res.* 73:210, 1993; Wang et al., *J Pharmacol. Exp. Ther.* 272:184, 1995), as well as the potassium channels that could serve as targets for the treatment of immunologic diseases and conditions and disorders of the nervous system and the gastrointestinal system. Consequently, the present invention also provides a method for treating diseases, conditions and disorders which respond to the inhibition of potassium channel function such as cardiac arrhythmias and various immunologic, nervous and gatrointestinal diseases using certain thiazolidinone and metathiazanone compounds.

The invention is particularly based on the discovery that thiazolidinone and metathiazanone compounds of the following formula (I), and pharmaceutically acceptable salts, esters, amides, complexes, chelates, hydrates, stereoisomers, crystalline or amorphous forms, metabolites, metabolic precursors or prodrugs thereof, are inhibitors of potassium channel function. In particular, these thiazolidinone and metathiazanone compounds have demonstrated activity against the human potassium channels/currents $I_{Kur}$, Kv1.5. As a result, these compounds are useful in the treatment inter alia, of cardiac arrhythmias and other diseases, conditions and disorders.

Thus, in a first aspect, the present invention concerns a method for treating diseases, conditions and disorders which respond to the inhibition of potassium channel function by using a compound having the formula (I) and pharmaceutically acceptable salts, esters, amides, complexes, chelates, hydrates, stereoisomers, crystalline or amorphous forms, metabolites, metabolic precursors or prodrugs thereof:

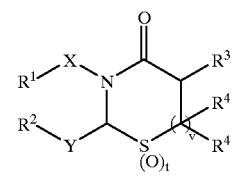

(I)

wherein, v is 0 or 1;

t is 0, 1, or 2;

X, in an orientation $R^1$—X—, is selected from —$(CR^4{}_2)_p$—; —$(CR^4{}_2)_mO(CR^4{}_2)_n$—; —$(CR^4{}_2)_mCH$=$CH(CR^4{}_2)_s$—; —$(CR^4{}_2)_mCH$≡$CH(CR^4{}_2)_s$—; —$(CR^4{}_2)_m$—A—$(CR^4{}_2)_m$—;

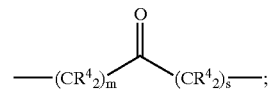

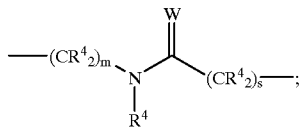

and

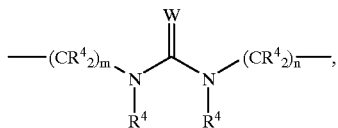

where p is an integer of 0 to 5, n is an integer of 2 to 4, m is an integer of 0 to 4 and s is an integer of 1 to 4; A is selected from an optionally substituted 3 to 7 membered carbocyclic ring and an optionally substituted 5 to 7 membered heterocyclic ring; each $R^4$ is independently selected from H, a lower alkyl, an aryl and a heteroaryl; W is selected from O and $NR^5$ where $R^5$ is selected from H, lower ally, aryl, C≡N and $NHR^4$;

$R^1$ is selected from H, an optionally substituted aryl and an optionally substituted heteroaryl;

Y, in an orientation $R^2$—Y—, is selected from —$(CR^4{}_2)_q$—; —$(CR^4{}_2)_m O(CR^4{}_2)_n$—; —$(CR^4{}_2)_m CH$=$CH(CR^4{}_2)_m$—; —$(CR^4{}_2)_m CH$≡$CH(CR^4{}_2)_m$—; —$(CR^4{}_2)_m$—A—$(CR^4{}_2)_m$— and a cycloalkyl, where q is an integer of 0 to 4 and m and n are as defined above;

$R^2$ is selected from H, an optionally substituted aryl and an optionally substituted heteroaryl; and $R^3$ is selected from H, optionally substituted lower alkyl, optionally substituted aryl, optionally substituted heteroaryl and —$NR^6R^7$, where $R^6$ is selected from H and optionally substituted lower alkyl; $R^7$ is H, optionally substituted lower alkyl, optionally substituted aryl, —$(SO_2)R^8$, —$COR^8$ and —C(O)NH—$R^4$, $R^8$ is selected from optionally substituted lower alkyl optionally substituted aryl and optionally substituted heteroaryl or $R^6$ and $R^7$ together with the nitrogen to which they are attached form a heteroaryl.

When v is 1, formula (I) relates to a class of metathiazanone compounds of the following formula, with the various variables as defined above:

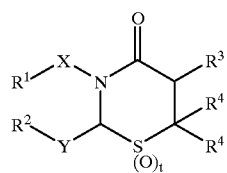

When v is 0, formula (I) relates to a class of thiazolidinone compounds of the following formula, with the various variables as defined above:

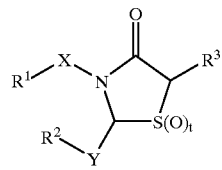

In a preferred aspect, the present invention concerns a method for treating diseases, conditions and disorders which respond to the inhibition of potassium channel function by using a compound having the formula (II) and pharmaceutically acceptable salts, esters, amides, complexes, chelates, hydrates, stereoisomers, crystalline or amorphous forms, metabolites, metabolic precursors or prodrugs thereof:

(II)

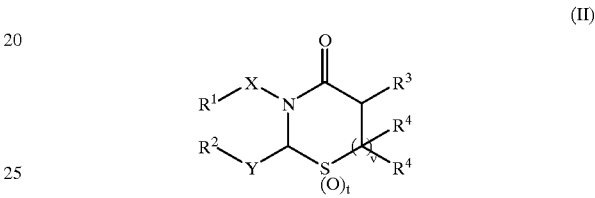

wherein, v is 0, or 1;

t is 0, 1, or 2;

X, in an orientation $R^1$—X—, is selected from —$(CR^4{}_2)_p$—; —$(CR^4{}_2)_m O(CR^4{}_2)_n$—; —$(CR^4{}_2)_m CH$=$CH(CR^4{}_2)_s$—; —$(CR^4{}_2)_m CH$≡$CH(CR^4{}_2)_s$—; and —$(CR^4{}_2)_m$—A—$(CR^4{}_2)_m$—; where p is an integer of 0 to 5, n is an integer of 2 to 4, m is an integer of 0 to 4 and s is an integer of 1 to 4; A is an optionally substituted 3 to 7 membered carbocyclic ring; each $R^4$ is independently selected from H, a lower alkyl, an aryl and a heteroaryl;

$R^1$ is selected from an optionally substituted aryl and an optionally substituted heteroaryl;

Y, in an orientation $R^2$—Y—, is selected from —$(CR^4{}_2)_q$—; —$(CR^4{}_2)_m O(CR^4{}_2)_n$—; —$(CR^4{}_2)_m CH$=$CH(CR^4{}_2)_m$—; —$(CR^4{}_2)_m CH$≡$CH(CR^4{}_2)_m$—; —$(CR^4{}_2)_m$—A—$(CR^4{}_2)_m$— and a cycloalkyl, where q is an integer of 0 to 4 and m and n are as defined above;

$R^2$ is selected from H, an optionally substituted aryl and an optionally substituted heteroaryl; and $R^3$ is selected from H, optionally substituted lower alkyl, optionally substituted aryl, optionally substituted heteroaryl and —$NR^6R^7$, where $R^6$ is selected from H and optionally substituted lower alkyl; $R^7$ is H, optionally substituted lower alkyl, optionally substituted aryl, —$(SO_2)R^8$, —$COR^8$ and —C(O)NH—$R^4$, $R^8$ is selected from optionally substituted lower alkyl, optionally substituted aryl and optionally substituted heteroaryl or $R^6$ and $R^7$ together with the nitrogen to which they are attached form a heteroaryl.

More preferred is a method for treating diseases, conditions and disorders which respond to the inhibition of potassium channel function by using a compound having the formula (III) and pharmaceutically acceptable salts, esters, amides, complexes, chelates, hydrates, stereoisomers, crystalline or amorphous forms, metabolites, metabolic precursors or prodrugs thereof:

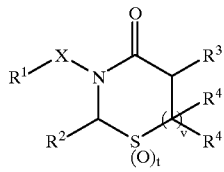

(III)

wherein, v is 0, or 1 t is 0, 1, or 2;

X, in an orientation $R^1$—X—, is selected from —$(CR^4_2)_p$—; —$(CR^4_2)_m CH=CH(CR^4_2)_s$—; —$(CR^4_2)_m CH\equiv CH(CR^4_2)_s$—; and —$(CR^4_2)_m$—A—$(CR^4_2)_m$—; where p is an integer of 0 to 5, n is an integer of 2 to 4, m is an integer of 0 to 4 and s is an integer of 1 to 3; A is an optionally substituted 3 to 7 membered carbocyclic ring; each $R^4$ is independently selected from H, a lower alkyl, an aryl and a heteroaryl;

$R^1$ is selected from an optionally substituted aryl and an optionally substituted heteroaryl;

$R^2$ is an optionally substituted phenyl; and $R^3$ is selected from H, optionally substituted lower alkyl, optionally substituted aryl, optionally substituted heteroaryl and —$NR^6R^7$, where $R^6$ is selected from H and optionally substituted lower alkyl; $R^7$ is H, optionally substituted lower alkyl, optionally substituted aryl, —$(SO_2)R^8$, —$COR^8$ and —$C(O)NH$—$R^4$, $R^8$ is selected from optionally substituted lower alkyl, optionally substituted aryl and optionally substituted heteroaryl or $R^6$ and $R^7$ together with the nitrogen to which they are attached form a heteroaryl.

In yet another aspect, the present invention is directed to certain compounds having the formula (IV) and pharmaceutically acceptable salts, esters, amides, complexes, chelates, hydrates, stereoisomers, crystalline or amorphous forms, metabolites, metabolic precursors or prodrugs thereof

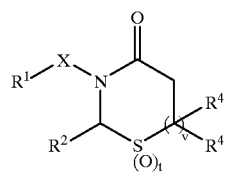

(IV)

wherein, v is 0, or 1;

t is 0, 1, or 2;

X, in an orientation $R^1$—X—, is selected from —$(CR^4_2)_p$—; —$(CR^4_2)(CH_2)$—; —$(CR^4_2)_m O(CR^4_2)_n$—; —$(CR^4_2)_m CH=CH(CR^4_2)_s$—; —$(CR^4_2)_p$—; —$(CR^4_2)_m CH\equiv CH(CR^4_2)_s$—; —$(CR^4_2)_m$—A—$(CR^4_2)_m$—;

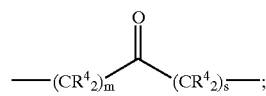

—$(CR^4_2)_m$—$NR^4$—$(CR^4_2)_n$—;

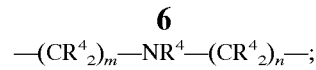

and

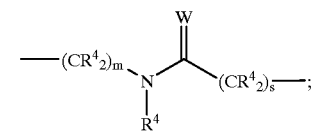

where p is an integer of 3 to 5, n is an integer of 2 to 4, m is an integer of 0 to 4 and s is an integer of 1 to 4; A is selected from an optionally substituted 3 to 7 membered carbocyclic ring and an optionally substituted 5 to 7 membered heterocyclic ring; each $R^4$ is independently selected from H, a lower alkyl, an aryl and a heteroaryl; W is selected from O and $NR^5$; $R^5$ is selected from H, lower alkyl, aryl, C—N and $NHR^4$;

$R^1$ is selected from H, an optionally substituted aryl and an optionally substituted heteroaryl;

$R^2$ is selected from an optionally substituted aryl and an optionally substituted heteroaryl, with the provisos that (1) when X is —$(CR^4_2)(CH_2)$— and $R^4$ is H then $R^1$ cannot be a monoalkylamino or dialkylamino substituted alkoxy substituted phenyl; (2) when X is —$(CR^4_2)_p$—, $R^4$ is H and p is 3 to 4 then $R^2$ cannot be a monoalkylamino or dialkylamino substituted alkoxy substituted phenyl; (3) when X is —$(CR^4_2)(CH_2)$— and $R^4$ is H then $R^1$ cannot be p-nitrophenyl, p-aminophenyl, (3-methoxy-4-ethoxyphenyl), or H and (4) when X is —$(CR^4CH_2)(CH_2)$— and $R^1$ is not H then $R^2$ cannot be pyridyl or indolyl.

In a preferred aspect, the present invention also concerns compounds having the formula (V) and pharmaceutically acceptable salts, esters, amides, complexes, chelates, hydrates, stereoisomers, crystalline or amorphous forms, metabolites, metabolic precursors or prodrugs thereof:

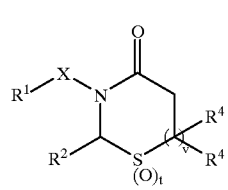

(V)

wherein, v is 0, or 1;

t is 0, 1, or 2;

X, in an orientation $R^1$—X—, is selected from —$CR^4_2)_p$—; —$(CR^4_2)(CH_2)$—; —$(CR^4_2)_m O(CR^4_2)_n$—; —$(CR^4_2)_m CH=CH(CR^4_2)_s$—; —$(CR^4_2)_m CH\equiv CH(CR^4_2)_s$—; and —$(CR^4_2)_m$—A—$(CR^4_2)_m$—; where p is an integer of 3 to 5, n is an integer of 2 to 4, m is an integer of 0 to 4 and s is an integer of 1 to 4; A is an optionally substituted 3 to 7 membered carbocyclic ring; each $R^4$ is independently selected from H, a lower alkyl, an aryl and a heteroaryl;

$R^1$ is selected from an optionally substituted aryl and an optionally substituted heteroaryl; and $R^2$ is selected from an optionally substituted aryl and an optionally substituted heteroaryl, with the provisos that (1)

when X is —(CR⁴₂)(CH₂)— and R⁴ is H then R¹ cannot be a monoalkylamino or dialkylamino substituted alkoxy substituted phenyl; (2) when X is —(CR⁴₂)ₚ—, R⁴ is H and p is 3 to 4 then R¹ cannot be a monoalkylamino or dialkylamino substituted alkoxy substituted phenyl; (3) when X is —(CR⁴₂)(CH₂)— and R⁴ is H then R¹ cannot be p-nitrophenyl, p-aminophenyl, (3-methoxy-4-ethoxyphenyl), or H and (4) when X is —(CR⁴₂)(CH₂)— and R¹ is not H, then R² cannot be pyridyl or indolyl.

More preferred are compounds having the formula (VI) and pharmaceutically acceptable salts, esters, amides, complexes, chelates, hydrates, stereoisomers, crystalline or amorphous forms, metabolites, metabolic precursors or pro-drugs thereof

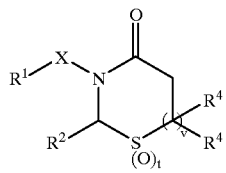

(VI)

wherein, v is 0, or 1;

t is 0, 1, or 2;

X, in an orientation R¹—X—, is selected from —(CR⁴₂)ₚ—; —(CR⁴₂)(CH₂)—; —(CR⁴₂)ₘCH=CH(CR⁴₂)ₛ—; —(CR⁴₂)ₘCH≡CH(CR⁴₂)ₛ—; and —(CR⁴₂)ₘ—A—(CR⁴₂)ₘ—; where p is an integer of 3 to 5, n is an integer of 2 to 4, m is an integer of 0 to 4 and s is an integer of 1 to 3; A is an optionally substituted 3 to 7 membered carbocyclic ring; each R⁴ is independently selected from H, a lower alkyl, an aryl and a heteroaryl;

R¹ is selected from an optionally substituted aryl and an optionally substituted heteroaryl; and R² is an optionally substituted phenyl, with the provisos that (1) when X is —(CR⁴₂)(CH₂)— and R⁴ is H then R¹ cannot be a monoalkylamino or dialkylamino substituted alkoxy substituted phenyl; (2) when X is —(CR⁴₂)ₚ—, R⁴ is H and p is 3 to 4 then R¹ cannot be a monoalkylamino or dialkylamino substituted alkoxy substituted phenyl; (3) when X is —(CR⁴₂)(CH₂)— and R⁴ is H then R¹ cannot be p-nitrophenyl, p-aminophenyl, (3-methoxy-4-ethoxyphenyl), or H and (4) when X is —(CR⁴₂)(CH₂)— and R¹ is not H, then R² cannot be pyridyl or indolyl.

Preferred R¹ substituents in formulae (I) through (VI) include phenyl; m- and p-methoxyphenyl; 3,4-methoxyphenyl; p-ethoxyphenyl; p-methylphenyl; p-ethylphenyl; 3,4-dimethylphenyl; 2,4-dichlorophenyl; p-chlorophenyl; p-bromophenyl; 3-bromo, 4-methoxyphenyl; indanyl and p-phenoxyphenyl. Preferred moieties for X in formulae (1) through (VI), in an orientation R¹—X—, include —CH₂CH₂—; —(CH₂)₃—; —(CH₂)₅—; —OCH₂CH₂—; —CHCH₂CH— (cyclopropyl); —CH₂C(O)—; —CH₂CH=CH— and —CH₂C≡C—. Preferred R² substituents in formulae (I) through (VI) include phenyl; m-methylphenyl; 3-methyl, 4-methoxyphenyl; 3,4-dimethylphenyl; p-dimethylaminophenyl; m-methoxyphenyl, p-methoxyphenyl; naphthyl; 3,5-dimethylphenyl; p-(1-pyrrolidinyl)phenyl; 3,4-dichlorophenyl; benzodioxane; 3-bromo, 4-methoxyphenyl; 3,5-dimethoxylphenyl; 1,3-benzodioxol-5-yl; 3-(1-methyl indolyl); 2-quinolyl; 2-(5-ethyl thienyl); 2-(5-ethyl furyl); 2-(4,5-dimethyl furyl); 3,4-dimethoxylphenyl; p-methylthiophenyl; indanyl; naphthyl; p-ethylphenyl; p-isopropylphenyl; 2,3-dimethyl, 4-methoxyphenyl; o-methoxyphenyl; 2,5-dimethyl, 4-methoxyphenyl; 3,4-dichlorophenyl; o-chlorophenyl; m-bromophenyl and 3-methylthio, 4-cyanophenyl. Preferred moieties for Y in formulae (I) and (II), in an orientation R²—Y—, include a simple covalent bond (i.e., —(CR⁴₂)ᵩ with q=0), —CH(C₆H₅)—; —CH₂—; —CH₂CH₂— and —CH(CH₃)—. Finally, the method, compound and compositions of the present invention are particularly directed to those instances involving formulae (1) through (VI) where v is 0 and t is 0.

The term "alkyl" as used alone or in combination herein refers to a straight or branched chain saturated hydrocarbon group containing from one to ten carbon atoms and the terms "C₁₋₆alkyl" and "lower alkyl" refer to such groups containing from one to six carbon atoms, such as methyl, ethyl, n-propyl, isopropyl, n-butyl, isobutyl, sec-butyl, tert-butyl and the like. The term "optionally substituted" when used in connection with an alkyl substituent refers to the replacement of up to two hydrogens, preferably on different carbon atoms with a radical selected form the group of lower alkoxy, phenyl, cyano, halo, trifluoromethyl, nitro, hydroxyl, alkanoyl, amino, monoalkyl amino and dialkylamino.

The term "alkoxy" as used alone or in combination herein refers to a straight or branched chain alkyl group covalently bonded to the parent molecule through an —O— linkage containing from one to ten carbon atoms and the terms "C₁₋₆alkoxy" and "lower alkoxy" refer to such groups containing from one to six carbon atoms, such as methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected form the group of lower alkyl, phenyl, cyano, halo, trifluoromethyl, nitro, hydroxyl, alkanoyl, amino, monoalkyl amino and dialkylamino.

The term "alkoxyalkyl" refers to an alkyl group substituted with an alkoxy group.

The term "haloalkyl" is a substituted alkyl, preferably a substituted lower alkyl, substituted with one or more halogen atoms, and preferably is a C₁ to C₄ alkyl substituted with one to three halogen atoms. One example of a haloalkyl is trifluoromethyl.

The term "alkanoyl" as used alone or in combination herein refers to an acyl radical derived from an alkanecarboxylic acid, particularly a lower alkanecarboxylic acid, and includes such examples as acetyl, propionyl, butyryl, valeryl, and 4-methylvaleryl.

The term "aminocarbonyl" means an amino-substituted carbonyl (carbamoyl or carboxamide) wherein the amino group can be a primary, secondary (mono-substituted amino) or tertiary amino (di-substituted amino) group preferably having as a substituent(s) a lower alkyl.

The term "carbocyclic ring" refers to stable, saturated or partially unsaturated monocyclic ring hydrocarbyls of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "carbocycloalkyl" refers to stable, saturated or partially unsaturated monocyclic, bridged monocyclic, bicyclic, and spiro ring hydrocarbyls of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. The term "optionally substituted" as it refers to "carbocycloalkyl" herein indicates that the carbocycloalkyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heterocyclic ring" as used herein refers to a stable, saturated, or partially unsaturated monocyclic ring system containing 5 to 7 ring members of carbon atoms and other atoms selected from nitrogen, sulfur and/or oxygen. Preferably, a heterocyclyl is a 5 or 6-membered monocyclic ring and contains one, two, or three heteroatoms selected from nitrogen, oxygen and/or sulfur. The term "optionally substituted" as it refers to "heterocyclic ring" herein indicates that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heterocyclyl" as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocyclyl is a 5 or 6-membered monocyclic ring or an 8–11 membered bicyclic ring which consists of carbon atoms and contains one, two, or three heteroatoms selected from nitrogen, oxygen or sulfur. The term "optionally substituted" as it refers to "heterocyclyl" herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclyl groups are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclyl group may be attached to the parent structure through a carbon atom or through any heteroatom of the heterocyclyl that results in a stable structure.

The term "heteroaryl" as used herein refers to a stable, aromatic monocyclic or bicyclic ring system containing carbon atoms and other atoms selected from nitrogen, sulfur and/or oxygen. Preferably, a heteroaryl is a 5 or 6-membered monocyclic ring (optionally benzofused) or an 8–11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino, cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heteroaryl groups are isoxazolyl, imidazolyl, thiazolyl, isothiazolyl, pyridyl, furyl, pyrimidinyl, pyrazolyl, pyridazinyl, furazanyl and thienyl. The heteroaryl group may be attached to the parent structure through a carbon atom or through any heteroatom of the heteroaryl that results in a stable structure.

The specific chemical nature of the optionally substituted heteroaryl groups for the terminal moieties $R^1$ and $R^2$ in the prior identified potassium channel inhibitor compounds is not narrowly critical and, as noted above, a wide variety of substituent groups are contemplated. Preferably, the substituents for the heteroaryl groups are selected such that the total number of carbon and hetero atoms comprising the substituted heteroaryls is no more than about 20.

The terms "halo" and "halogen" as used herein to identify substituent moieties, represent fluorine, chlorine, bromine or iodine, preferably chlorine or fluorine.

The term "aryl" when used alone or in combination refers to an unsubstituted or optionally substituted monocyclic or bicyclic aromatic hydrocarbon ring system. Preferred are optionally substituted phenyl or naphthyl groups. The aryl group may optionally be substituted at one or more substitutable ring positions by one or more groups independently selected from optionally substituted alkyl (preferably an optionally substituted lower alkyl), optionally substituted alkoxy (preferably an optionally substituted lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Preferably, the aryl group is phenyl optionally substituted with up to four and usually with one or two groups, preferably selected from $C_{1-6}$alkyl, $C_{1-6}$alkoxy, as well as cyano, trifluoromethyl and halo. Two alkyl or two alkoxy substituents on a substituted phenyl may form a closed ring structure between the meta and para positions on the phenyl, thus forming an indanyl, benzodioxane, benzopyran and the like groups.

The term "aralkyl" alone or in combination refers to an alkyl radical as defined above in which one hydrogen atom is replaced by an aryl radical as defined above, and includes benzyl, and 2-phenylethyl.

The term "alkoxycarbonyl" alone or in combination means a radical of the formula —C(O)—alkoxy, in which alkoxy is as defined above.

The term "alkylcarbonyloxy" alone or in combination means a radical of the formula —O—C(O)—alkyl, in which alkyl is as defined above.

The term "alkenyl" means a two to seven carbon, straight or branched hydrocarbon containing one or more double bonds, preferably one or two double bonds. Examples of alkenyl include ethenylene, propenylene, 1,3- butadienyl, and 1,3,5-hexatrienyl.

Unless otherwise defined, the term "optionally substituted" as used herein, refers to the substitution of a ring system at one or more positions with one or more groups selected from: $C_{1-6}$alkyl, $C_{1-6}$alkoxy, an optionally substituted phenyl, cyano, halo, trifluoromethyl, $C_{1-8}$alkoxycarbonyl, $C_{1-6}$alkyl carbonyloxy, mono- & bis-($C_{1-6}$alkyl)-carboxamide, $C_{1-6}$alkyl amido, nitro, and mono- & bis-($C_{1-6}$alkyl)-amino.

The term "treating" as used herein, describes the management and care of a patient afflicted with a condition, disease or disorder for which the administration of a compound in accordance with the present invention alters the action or activity of a potassium channel to prevent the onset of symptoms or complications associated with the condition, disease or disorder, to alleviate the symptoms or complications caused by the condition, disease or disorder, or to eliminate the condition, disease or disorder altogether.

Thiazolidinone and metathiazanone compounds of the previous formulae useful as potassium channel inhibitors in accordance with the present invention can be prepared in accordance with the following general procedure:

A mixture of an amine (1 equivalent), an aldehyde (2 equivalents), and a mercaptoacid (3 equivalents) in benzene or toluene is heated to a temperature in the range of 80° C. to 100°. In some cases an amine hydrochloride can be used. In those instances, about 1–1.5 equivalents of $NEt_3$ also are added. After 2–24 hr, the reaction mixture is allowed to cool to room temperature and the solvent can be removed under reduced pressure. The crude product is dissolved in EtOAc and washed with saturated $NaHCO_3$, 1 N HCl, and saturated NaCl. The organic layer is dried ($Na_2SO_4$), filtered and concentrated. Purification by column chromatography on silica gel gives the desired thiazolidinone or metathiazanone product. Oxidation of a thiazolidinone or a metathiazanone to the corresponding sulfoxide or sulfone is readily accomplished by treatment with meta-chloroperbenzoic acid at 0° C.

It is recognized that there is at least one chiral center in the compounds used within the scope of the present invention and thus such compounds will exist as various stereoisomeric forms. Applicants intend to include all the various stereoisomers within the scope of the invention. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention.

The present invention also encompasses the pharmaceutically acceptable salts, esters, amides, complexes, chelates, hydrates, crystalline or amorphous forms, metabolites, metabolic precursors or prodrugs of the compounds of formulae (I), (II), (III), (IV), (V) and (VI). Pharmaceutically acceptable esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmakokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, *Design of Prodrugs*, (1985). Those skilled in the art are well-versed in the preparation of prodrugs and are well-aware of its meaning.

As will be recognized by those skilled in the art, certain compounds used in accordance with the present invention can be used in their neat form or in the form of pharmaceutically-acceptable salts derived from inorganic or organic acids. Examples of acids which may be employed to form pharmaceutically acceptable acid addition salts of compounds of the present invention include such inorganic acids as hydrochloric acid, sulphuric acid and phosphoric acid and such organic acids as oxalic acid, maleic acid, succinic acid and citric acid. These salts thus include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Also, any basic nitrogen-containing groups in compounds of the invention can be quaternized with such agents as lower alkyl halides, such as methyl, ethyl, propyl, and butyl chlorides, bromides and iodides; dialkyl sulfates, like dimethyl, diethyl, dibutyl and diamyl sulfates, long chain halides such as decyl, lauryl, myristyl and stearyl chlorides, omides and iodides, aralkyl halides like benzyl and phenethyl bromides and others. Water or oil soluble or dispersible products are thereby generally obtained.

The pharmaceutically acceptable salts of compounds used in accordance with the present invention also can exist as various solvates, such as with water, methanol, ethanol, dimethylformamide, ethyl acetate and the like. Mixtures of such solvates also can be prepared. Such solvates are within the scope of the present invention.

The pharmacological profile of the potassium channel inhibitory activity of thiazolidinone and metathiazanone compounds falling within the teachings of the present invention can be readily assessed by those skilled in the art using routine experimentation, such as the procedures and techniques illustrated in the examples which follow. Assays for assessing the activity of particular compounds may employ cells stably transfected to express a specific potassium channel, as well as native mammalian cells. In particular, cells stably transfected to express a specific potassium channel, which have been treated with a voltage dependent fluorescent dye, such as bis-(1,3-dibutylbarbituric acid) trimethine oxonol, can be used to gauge the inhibitory activity of potassium channel inhibitor compounds, possibly in comparison to known inhibitors. Alternatively, such cells can be primed with a detectible species, such as $^{86}Rb$, and then challenged with a particular compound, under conditions otherwise suitable for activating the potassium channel, to assess the potassium inhibitory activity of the compound. The potassium channel inhibitory activity of a compound also can be determined using isolated mammalian cells and the whole cell configuration of the known patch clamp technique (Hamill et al., *Pflugers Archiv* 391:85, 1981). These and other known techniques can be readily employed by those skilled in the art to assess the activity level of the potassium channel inhibitor compounds contemplated by the present invention.

Thiazolidinone and metathiazanone compounds suitable for use within the scope of the present invention may be administered by a variety of routes including orally, parenterally, sublingually, intranasally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intracardiac injection, or infusion techniques. Topical administration may also involve the use of transdermal administration such as transdermal patches or iontophoresis devices.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,2-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

Thiazolidinone and metathiazanone compounds contemplated for use within the scope of the present invention can also be administered in the form of liposomes. As is known in the art, liposomes are generally derived from phospholipids or other lipid substances. Liposomes are formed as mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p.33, et seq.

To select preferred compounds from less preferred compounds, one uses by example the in vitro assays detailed under the sub-heading BioAssays hereafter. Typically, a preferred compound will produce half maximal blocking activity at a concentration ranging from about 10 nM to about 1 $\mu$M in the in vitro assays described. One of ordinary skill will recognize that the final and optimum dose and regimen will be determined empirically for any given drug.

Total daily dose administered to a host in single or divided doses may be an amount, for example, from 0.001 to 100 mg of active ingredient per kg body weight on a daily basis and more usually 0.01 to 10 mg/kg/day. Dosage unit compositions may contain such amounts of submultiples thereof to make up the daily dose. It is anticipated that a therapeutically effective serum concentration of active ingredient will be 10 nM to 10 $\mu$M (5 ng/ml to 5 $\mu$g/ml).

The amount of active ingredient that may be combined with carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, and diet of the patient, the time of administration, the route of administration, the rate of excretion, whether a drug combination is used, and the severity of the particular disease.

The present invention is explained in greater detail in the Examples which follow. These examples are intended as illustrative of the invention, and are not to be taken as limiting thereof Unless otherwise indicated, all references to parts and percentages are based on weight and all temperatures are expressed in degrees Celsius. The scope of the invention is not construed as merely consisting of the following examples.

EXAMPLES

Compound Preparation

All solvents and reagents were purchased from commercial suppliers and were used without further purification. Analytical thin layer chromatography was performed on Whatman Inc. 60 silica gel plates (0.25 mm thickness). Compounds were visualized under UV lamp or by developing with $KMnO_4/KOH$,. Flash chromatography was done using silica gel from Selectro Scientific (particle size 32–63). $^1H$ NMR and $^{13}C$ NMR spectra were recorded at 300 MHz and 75.5 MHz, respectively.

Preparation 1

A mixture of m-anisaldehyde (0.74 ml; 6.1 mmol), mercaptoacetic acid (0.64 ml; 9.2 mmol), and 4-methoxyphenethylamine (0.46 g; 3.1 mmol) in benzene (10 ml) was heated at 80° C. for 2.5 h. The reaction mixture was allowed to cool to room temperature and the solvent was removed under reduced pressure. The residue was diluted with EtOAc (30 ml) and the organic phase was washed with saturated $NaHCO_3$ (50 ml), 1 N HCl (50 ml) and saturated NaCl (50 ml), dried ($Na_2SO_4$), filtered and concentrated. Column chromatography on silica gel provided the product (Entry 1 of Table 1) as a colorless oil (0.87 g; 83%). $R_f$(silica gel): 0.30 (70% hexane: 30% EtOAc); $^1$HNMR (300 MHz, $CDCl_3$) 7.28 (t, J=7.8 Hz, 1H), 7.02 (d, J=8.7 Hz, 2H), 6.89–6.73 (m, 5H), 5.28 (s, 1H), 3.91–3.84 (m, 1H), 3.79 (s, 3H), 3.28 (s, 3H), 3.78 (d, J=15.0 Hz, 1H), 3.66 (d, J=15.0 Hz, 1H), 2.92–2.76 (m, 2H), 2.68–2.59 (m, 1H); $^{13}C$ NMR (75.5 MHz, $CDCl_3$) 171.5, 160.3, 158.5, 141.0, 130.5, 130.2, 129.8 (two carbons), 119.4, 114.7, 114.1 (two carbons), 112.6, 63.9, 55.3, 55.2, 44.7, 32.8, 32.3.

Preparation 2

The procedure as described for Preparation 1 was repeated using p-anisaldehyde, mercaptoacetic acid and 2-(p-tolyl)ethylamine as starting materials. Yield (Entry 2 of Table 1): 56%. $R_f$ (silica gel): 0.44 (70% hexane: 30% EtOAc); $^1$H NMR (300 MHz, $CDCl_3$) 7.15 (d, J=8.7 Hz, 1H), 7.08 (d, J=7.8 Hz, 1H), 6.98 (d, J=7.8 Hz, 1H), 6.88 (d, J=8.7 Hz, 1H), 5.31 (s, 1H), 3.85–3.80 (m, 1H), 3.81 (s, 3H), 3.77 (d, J=1.5 and 15.6 Hz, 1H), 3.67 (d, J=15.6 Hz, 1H), 2.91–2.76 (m, 2H), 2.66–2.56 (m, 1H), 2.31 (s, 3H).

Preparation 3

The procedure as described for Preparation 1 was repeated using 4-(1-pyrrolidino)benzaldehyde, mercaptoacetic acid, and 4-methoxyphenethylamine as starting materials. Yield (Entry 3 of Table 1): 86%. $R_f$ (silica gel): 0.38 (70% hexane; 30% EtOAc); $^1$H NMR (300 MHz, $CDCl_3$) 7.08 (d, J=8.7 Hz, 1H), 7.02 (d, J=8.7 Hz, 1H), 6.81 (d, J=8.7 Hz, 1H), 6.51 (d, J=8.7 Hz, 1H), 5.31 (s, 1H), 3.82–3.75 (m, 1H), 3.77 (s, 3H), 3.75 (dd, J=1.8 and 15.3 Hz, 1H), 3.65 (d, J=15.3 Hz, 1H), 3.28 (t, J=6.6 Hz, 4H), 2.94–2.74 (m, 2H), 2.63–2.54 (m, 1H), 2.06–1.92 (M, 4H); $^{13}C$ NMR (75.5 MHz, $CDCl_3$) 171.1, 158.4, 148.6, 130.8, 129.8 (two carbons), 128.7 (two carbons), 124.6, 114.0 (two carbons), 111.7 (two carbons), 64.3, 55.2, 47.5 two carbons), 44.3, 33.1, 32.3, 25.4 (two carbons).

Preparation 4

The procedure as described for Preparation 1 was repeated using 1,4-dioxan-6-carboxyaldehyde, mercaptoacetic acid, and 4-methoxyphenethylamine as starting materials. Yield (Entry 4 of Table 1): 98%. $R_f$ (silica gel): 0.26 (70% hexane: 30% EtOAc); $^1$HNMR (300 MHz, $CDCl_3$) 7.02 (d, J=8.7 Hz, 2H), 6.84–6.80 (m, 3H), 6.73 (d, J=2.1 Hz, 1H), 6.67 (dd, J=2.1 and 8.4 Hz, 1H), 5.22 (d, J=1.2 Hz, 1H), 4.24 (s, 3H), 3.87–3.80 (m, 1H), 3.78 (s, 3H), 3.74 (dd, J=1.5 Hz and 15.3 Hz, 1H), 3.63 (d, J=15.3 Hz, 1H), 2.91–2.74 (m, 2H), 2.68–2.57 (m, 1H); $^{13}C$ NMR (75.5 MHz, $CDCl_3$) 171.1, 158.5, 144.4, 144.0, 132.5, 130.6, 129.8 (two carbons), 120.3, 117.7, 116.1, 114.1 (two carbons), 64.3 (two carbons), 63.6, 55.2, 44.5, 32.8, 32.3.

Preparation 5

The procedure as described for Preparation 1 was repeated using 3,4-dimethoxybenzaldehyde, mercaptoacetic acid, and 4-methoxyphenethylamine as starting materials. Yield (Entry 5 of Table 1): 16%. $R_f$(silica gel): 0.20 (70% hexane: 30% EtOAc); $^1$HNMR (300 MHz, $CDCl_3$) 7.00 (d, J=8.7 Hz, 2H), 6.82–6.72 (m, 5H), 5.29 (s, 1H), 3.88 (s, 3H), 3.85 (s, 3H), 3.80–3.78 (m, 1H), 3.77 (s, 3H), 3.74 (dd, J=1.8 and 15.3 Hz, 1H), 3.66 (d, J=15.3 Hz, 1H), 2.91–2.74 (m, 2H), 2.66–2.56 (m, 1H); $^{13}C$ NMR (75.5 MHz, $CDCl_3$) 171.2, 158.5, 150.0, 149.8, 131.3, 130.6, 129.8 (two carbons), 120.2, 114.1 (two carbons), 110.9, 109.9, 64.1, 56.0, 55.9, 55.2, 44.5, 32.9, 32.3.

Preparation 6

The procedure as described for Preparation 1 was repeated using benzaldehyde, mercaptoacetic acid, and 4-methoxyphenethylamine as starting materials. Yield (Entry 31 of Table 1): 99% $R_f$(silica gel): 0.26 (80% hexane: 20% EtOAc); $^1$NMR (300 MHz, $CDCl_3$) 7.37–7.35 (m, 3H), 7.23–7.20 (m, 2H), 7.01 (d, J=8.7 Hz, 2H), 6.95 (d, J=8.7 Hz, 2H), 5.32 (s, 1H), 3.88–3.82 (m, 1H), 3.77 (s, 3H), 3.77 (d, J=15.3 Hz, 1H), 3.66 (d, J=15.3 Hz, 1H), 2.90–2.75 (m, 2H), 2.65–2.56 (m, 1H); $^{13}C$ NMR (75.5 MHz, $CDCl_3$) 171.3, 158.5, 139.5, 130.5, 129.8 (two carbons), 129.3, 129.1 (two carbons), 127.3 (two carbons), 114.1 (two carbons), 64.0, 55.2, 44.7, 32.8, 32.3.

Preparation 7

The procedure as described for Preparation 1 was repeated using cyclohexane carboxyaldehyde, mercapotacetic acid, and 4-methoxyphenethylamine as starting materials. Yield (Entry 32 of Table 1): 98% $R_f$ (silica gel): 0.45 (80% hexane: 20% EtOAc); $^1$H NMR (300 MHz, $CDCl_3$) 7.12 (d, J=8.4 Hz, 2H), 6.82 (d, J=8.4 Hz, 2H), 4.41 (s, 1H), 3.95–3.86 (m, 1H), 3.76 (s, 3H), 3.48 (d, J=15.6 Hz, 1H), 3.56 (d, J=15.6 Hz, 1H), 3.13–3.04 (m, 1H), 2.89–2.71 (m, 2H), 1.85–1.65 (m, 4H), 1.39–1.10 (m, 7H); $^{13}C$ NMR (75.5 MHz, $CDCl_3$) 171.5, 158.5, 130.5, 129.7 (two carbons), 114.1 (two carbons), 67.2, 55.2, 44.6, 41.0, 32.4 (two carbons), 29.1, 26.0 (two carbons), 25.3, 24.0.

Preparation 8

The procedure as described for Preparation 1 was repeated using 3,4-dimethylbenzaldehyde, mercaptoacetic acid, and 4-methoxyphenethylamine as starting materials. Yield (Entry 52 of Table 1): 95%. $R_f$ (silica gel): 0.48 (70% hexane: 30% EtOAc); $^1$H NMR (300 MHz, $CDCl_3$) 7.12 (d, J=7.5 Hz, 1H), 7.03 (d, J=8.7 Hz, 2H), 6.97 (s, 1H), 6.94 (d, J=8.7 Hz, 1H), 5.29 (d, J=1.2 Hz, 1H), 3.91–3.83 (m, 1H), 3.78 (s, 3H), 3.77 (dd, J=1.8 and 15.3 Hz, 1H), 3.66 (d, J=15.3 Hz, 1H), 2.91–2.75 (m, 2H), 2.68–2.59 (s, 1H), 2.26 (s, 6H); $^{13}C$ NMR (75.5 MHz, $CDCl_3$) 171.3, 158.5, 137.9, 137.5, 136.8, 130.6, 130.2, 129.8 (two carbons), 128.2, 124.7, 114.1 (two carbons), 63.8, 55.2, 44.5, 32.8, 32.3, 1.7, 19.5.

Preparation 9

A mixture of, 3,4-dimethylbenzaldehyde (0.190 g; 1.42 mmol), mercaptoacetic acid (0.14 ml; 2.0 ml), 2-(4-methoxyphenoxy)ethylamine hydrochloride (0.136 g; 0.668 mmol), and $NEt_3$(0.11 ml; 0.79 mmol) in benzene (6 ml) was heated at 80° C. for 6 h. The reaction mixture was allowed to cool to room temperature and the solvent was removed under reduced pressure. The residue was diluted with EtOAc (20 ml) and the organic phase was washed with saturated $NaHCO_3$ (20 ml), 1 N HCl (20 ml) and saturated NaCl (30 ml), dried $Na_2SO_4$), filtered and concentrated. Column chromatography on silica gel provided the product (Entry 53 of Table 1): as a colorless oil (0.229 g; 96%). $R_f$(silica gel): 0.56 (60% hexane: 40% EtOAc); $^1$H NMR (300 MHz, $CDCl_3$) 7.14 (d, J=7.2 Hz, 1H), 7.07 (s, 1H), 7.06 (d, J=7.2 Hz, 1H), 6.84–6.76 (m, 4H), 5.84 (d, J=0.9 Hz, 1H), 4.14–4.06 (m, 1H), 3.98–3.88 (m, 2H), 3.80 (dd, J=1.8 and 15.6 Hz, 1H), 3.76 (s, 3H), 3.70 (d, J=15.6 Hz, 1H), 3.15–3.05 (m, 1H), 2.26 (s, 6H); $^{13}$C NMR (75.5 MHz, $CDCl_3$) 171.6, 154.3, 152.5, 137.9, 137.5, 136.8, 130.3, 128.5, 124.9, 115.4 (two carbons), 114.8 (two carbons), 66.3, 64.5, 55.7, 42.3, 32.7, 19.7, 19.4.

Preparation 10

The procedure as described for Preparation 9 was repeated using 3,4-dimethylbenzaldehyde, mercaptoacetic acid, and 4-nitrophenethylamine hydrochloride as starting materials. Yield (Entry 65 of Table 1): 78% $R_f$ (silica gel): 0.31 (70% hexane: 30% EtOAc); $^1$H NMR (300 MHz, $CDCl_3$) 8.12 (d, J=8.7 Hz, 2H), 7.25 (, J=8.7 Hz, 2H), 7.13 (d, J=7.5 Hz, 1H), 7.00 (s, 1H), 6.97 (d, J=7.5 Hz, 1H), 5.37 (d, J=1.2 Hz, 1H), 3.89–3.80 (m, 1H), 3.79 (dd, J=1.2 and 15.6 Hz, 1H), 3.65 (d, J=15.6 Hz, 1H), 3.06–2.89 (m, 2H), 2.81–2.72 (m, 1H), 2.26 (s, 6H); $^{13}$C NMR (75.5 MHz, $CDCl_3$) 171.5, 147.0, 146.2, 138.3, 137.8, 136.4, 130.4, 129.7, (two carbons), 128.2, 124.6, 123.8 (two carbons), 63.8, 43.8, 33.1, 32.7, 19.7, 19.4.

Preparation 11

The procedure as described for Preparation 9 was repeated using 3,4-dimethylbenzaldehyde, mercaptoacetic acid, 2-aminoacetophenone hydrochloride as starting materials. Yield (Entry 78 of Table 1): 44% $R_f$ (silica gel): 0.64 (60% hexane: 40% EtOAc); $^1$H NMR (300 MHz, $CDCl_3$) 7.84 (d J=7.5 Hz, 2H), 7.56 (t, J=7.2 Hz, 1H), 7.421 (t, J=7.5 Hz, 2H), 7.12–7.03 (m, 3H), 5.86 (s, 1H), 5.20 (d, J=17.7 Hz, 1H), 3.95–3.78 (m, 3H), 2.24 (s, 6H); $^{13}$C NMR (75.5 MHz, $CDCl_3$) 193.0, 172.4, 138.3, 137.7, 135.5, 134.8, 133.9, 130.4, 128.82 (two carbons), 128.77, 128.0 (two carbons), 125.2, 63.8, 48.8, 32.8, 19.7, 19.4.

Preparation 12

The procedure as described for Preparation 9 was repeated using 3,4-dimethylbenzaldehyde, mercaptoacetic acid, and 3-phenyl-allylamine hydrochloride as starting materials. Yield (Entry 81 of Table 1): 34% $R_f$ (silica gel): 0.49 (70% hexane: 30% EtOAc); $^1$H NMR (300 MHz, $CDCl_3$) 7.31–7.25 (m, 5H), 7.15 (d, J=7.5 Hz, 1H), 7.07 (s, 1H), 7.02 (d, J=7.5 Hz, 1H), 6.29 (d, J=15.9 Hz, 1H), 6.01 (ddd, J =5.1, 8.1, and 15.9 Hz, 1H), 5.60 (d, J=1.8 Hz, 1H), 4.55 (ddd, J=1.8, 5.1, and 15.0 Hz, 1H), 3.87 (dd, J=1.8 and 15.6 Hz, 1H), 3.73 (d, J=15.6 Hz, 1H), 3.35 (dd, J=8.1 and 15.0 Hz, 1H), 2.65 (s, 6H); $^{13}$C NMR (75.5 MHz, $CDCl_3$) 171.2, 138.0, 137.6, 136.7, 136.3, 134.4, 130.3, 128.67 (two carbons), 128.30, 128.0, 126.5 (two carbons), 124.69, 122.5, 63.1, 44.7, 33.0, 19.7, 19.4.

Preparation 13

The procedure as described for Preparation 9 was repeated using 3,4-dimethylbenzaldehyde, mercaptoacetic acid, and 3-phenylpropargylamine hydrochloride as starting materials. Yield (Entry 82 of Table 1): 48% $R_f$ (silica gel): 0.60 (70% hexane: 30% EtOAc); $^1$H NMR (300 MHz, $CDCl_3$) 7.41–7.26 (m, 5H), 7.18–7.10 (m, 3H), 5.85 (d, J=1.8 Hz, 1H), 4.84 (d, J=17.4 Hz, 1H), 3.86 (dd, J=1.8 and 15.3 Hz, 1H), 3.80 (d, J=15.3 Hz, 1H), 3.54 (d, J=17.4 Hz, 1H), 2.27 (s, 6H); $^{13}$C NMR (75.5 MH, $CDCl_3$) 170.9, 139.2, 137.6, 135.9, 131.9, (two carbons), 130.3, 128.7, 128.6, 128.4 (two carbons), 125.0, 122.4, 84.6, 82.2, 62.9, 33.1, 32.9, 19.7, 19.5.

Using the principles and techniques of Preparations 1 through 13, and appropriate starting materials, which will be well-understood by those skilled in the art, a variety of other compounds falling within the scope of the present invention can be synthesized. In this regard, thiazolidinone compounds ( compounds of formula (I) with v=0 and t=0) listed in the following Table 1 can be synthesized.

TABLE 1

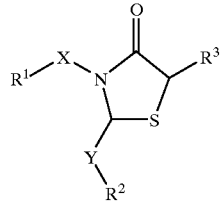

| Entry | R$^1$—X— | R$^2$—Y— | R$^3$— |
|---|---|---|---|
| 1 | 2-(4-methoxyphenethyl) | 3-methoxyphenyl | H |
| 2 | 2-(4-methylphenethyl) | 4-methoxyphenyl | H |
| 3 | 2-(4-methoxyphenethyl) | 4-pyrrolidinylphenyl | H |
| 4 | 2-(4-methoxyphenethyl) | 4-benzodioxanyl | H |
| 5 | 2-(4-methoxyphenethyl) | 3,4-dimethoxyphenyl | H |
| 6 | 2-(4-methoxyphenethyl) | 4-benzodioxolanyl | H |
| 7 | 2-(4-methoxyphenethyl) | 3-methyl-4-methoxyphenyl | H |

TABLE 1-continued

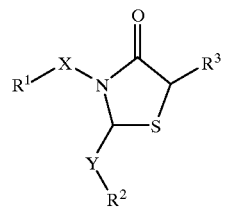

| Entry | R¹—X— | R²—Y— | R³— |
|---|---|---|---|
| 8 | 2-(3-methoxyphenethyl) | 4-benzodioxolanyl | H |
| 9 | 2-phenethyl | 3-methoxyphenyl | H |
| 10 | 2-(4-methoxyphenethyl) | 4-ethylphenyl | H |
| 11 | 2-(4-methoxyphenethyl) | 4-isopropoxyphenyl | H |
| 12 | 2-(4-methoxyphenethyl) | 4-methylthiophenyl | H |
| 13 | 2-(4-chlorophenethyl) | 4-methoxyphenyl | H |
| 14 | 2-(4-methoxyphenethyl) | 4-isopropylphenyl | H |
| 15 | 2-(4-methoxyphenethyl) | 4-benzoxyphenyl | H |
| 16 | 2-(3-methoxyphenethyl) | 4-(N-acetyl)aminophenyl | H |
| 17 | 2-(4-methoxyphenethyl) | 4-dimethylaminophenyl | H |
| 18 | 2-(4-ethylphenethyl) | 3-methoxyphenyl | H |
| 19 | 2-(4-phenoxyphenethyl) | 2-methoxyphenyl | H |
| 20 | 2-(3,4-dimethoxyphenethyl) | 4-ethylphenyl | H |
| 21 | 2-(4-methoxyphenethyl) | 3,4-dichlorophenyl | H |
| 22 | 2-(3,4-dimethoxyphenethyl) | 4-dimethylaminophenyl | H |
| 23 | 2-(4-methoxyphenethyl) | 3,4-difluorophenyl | H |
| 24 | 2-(3-bromo-4-methoxyphenethyl) | 3-methoxyphenyl | H |
| 25 | 2-(2,4-dichlorophenethyl) | 3-methoxyphenyl | H |
| 26 | 2-(4-methoxyphenethyl) | 3-benzodioxolanyl | H |
| 27 | 2-(4-methoxyphenethyl) | 2,3-dimethyl-4-methoxyphenyl | H |
| 28 | 2-(4-methoxyphenethyl) | β-naphthyl | H |
| 29 | 2-(4-methoxyphenethyl) | 2-thiophenyl | H |
| 30 | 2-(4-methoxyphenethyl) | 3-quinolinyl | H |
| 31 | 2-(4-methoxyphenethyl) | phenyl | H |
| 32 | 2-(4-methoxyphenethyl) | cyclohexyl | H |
| 33 | 2-(4-methoxyphenethyl) | benzyl | H |
| 34 | 2-(4-methoxyphenethyl) | 3,5-dimethoxyphenyl | H |
| 35 | 3-phenpropyl | 4-dimethylaminophenyl | H |
| 36 | 4-methoxybenzyl | 3-methoxyphenyl | H |
| 37 | 3-phenpropyl | 4-ethylphenyl | H |
| 38 | 4-phenbutyl | 2-methoxyphenyl | H |
| 39 | n-hexyl | 4-dimethylaminophenyl | H |
| 40 | 4-methoxybenzyl | 2-chlorophenyl | H |
| 41 | 2-(4-methoxyphenethyl) | 3-methoxyphenyl | Me |
| 42 | 2-(4-methoxyphenethyl) | 4-ethylphenyl | Me |
| 43 | 2-(4-chlorophenethyl) | 4-ethylphenyl | Me |
| 44 | 2-(4-methoxyphenethyl) | 3-methyl-4-methoxyphenyl | Me |
| 45 | 2-(4-methoxyphenethyl) | 4-benzodioxanyl | Me |
| 46 | 2-(4-bromophenethyl) | 4-methoxyphenyl | H |
| 47 | 2-(4-ethylphenethyl) | 3-methylphenyl | H |
| 48 | 2-(-4-ethoxyphenethyl) | 4-benzodioxolanyl | H |
| 49 | 2-phenethyl | 3-methyl-4-methoxyphenyl | H |
| 50 | 4-methoxybenzyl | 3-methyl-4-methyoxyphenyl | H |
| 51 | 2-phenoxyethyl | phenyl | H |
| 52 | 2-(4-methoxyphenethyl) | 3,4-dimethylphenyl | H |
| 53 | 2-(4-methoxyphenoxyethyl) | 3,4-dimethylphenyl | H |
| 54 | 2-(3-methoxyphenethyl) | 4-benzodioxanyl | H |
| 55 | 2-(3-methoxyphenethyl) | 2,4-dichlorophenyl | H |
| 56 | n-pentyl | 3-methoxyphenyl | H |
| 57 | benzyl | 3,4-dimethylphenyl | H |
| 58 | 2-(3-methoxyphenethyl) | 4-benzodioxanyl | H |
| 59 | 2-(3-methoxyphenethyl) | 4-benzodioxolanyl | H |
| 60 | 4-phenbutyl | 3,4-dimethylphenyl | H |
| 61 | 2-(3-methoxyphenethyl) | 3,4-dichlorophenyl | H |
| 62 | 2-(3-methoxyphenethyl) | 3-methylphenyl | H |
| 63 | 2-(3-methoxyphenethyl) | 3-bromo-4-methoxyphenyl | H |
| 64 | 2-(3-methoxyphenethyl) | β-naphthyl | H |
| 65 | 2-(4-nitrophenethyl) | 3,4-dimethylphenyl | H |
| 66 | 2-(3-methoxyphenethyl) | 2,3-dimethyl-4-methoxyphenyl | H |
| 67 | 2-(4-methoxyphenethyl) | 5-ethyl-2-thiophenyl | H |
| 68 | 2-(3-methoxyphenethyl) | 3-benzodioxolanyl | H |
| 69 | 2-phenoxyethyl | 4-benzodioxolanyl | H |
| 70 | 2-phenoxyethyl | 3,4-dimethylphenyl | H |
| 71 | 2-phenoxyethyl | 4-ethylphenyl | H |
| 72 | 2-(4-methylphenethyl) | 4-benzodioxolanyl | H |

TABLE 1-continued
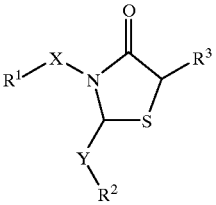
| Entry | R¹—X— | R²—Y— | R³— |
|---|---|---|---|
| 73 | 2-(4-methylphenethyl) | 3,4-dimethylphenyl | H |
| 74 | 2-(4-methylphenethyl) | 4-ethylphenyl | H |
| 75 | 2-phenoxyethyl | 5-ethyl-2-thiophenyl | H |
| 76 | 2-phenoxyethyl | 5-methyl-2-thiophenyl | H |
| 77 | n-hexyl | 3-methoxyphenyl | H |
| 78 | 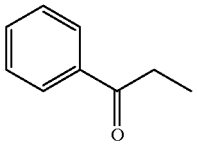 | 3,4-dimethylphenyl | H |
| 79 | 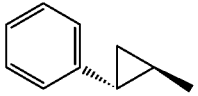 | 4-benzodioxolanyl | H |
| 80 | 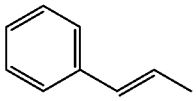 | 3-methoxyphenyl | H |
| 81 | 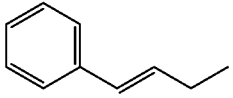 | 3,4-dimethylphenyl | H |
| 82 | 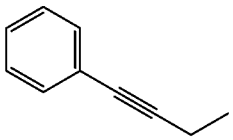 | 3,4-dimethylphenyl | H |
| 83 | 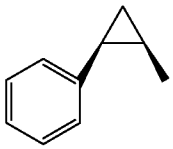 | 4-ethylphenyl | H |
| 84 | 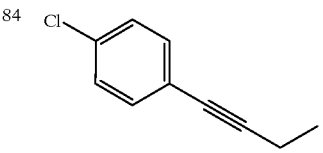 | 4-benzodioxolanyl | H |

TABLE 1-continued

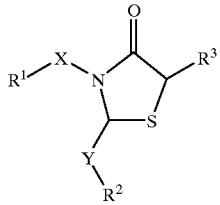

| Entry | R¹—X— | R²—Y— | R³— |
|---|---|---|---|
| 85 | MeO-C₆H₄-CH=CH-CH₂- (4-methoxycinnamyl structure) | 3-methyl-4-methoxyphenyl | H |
| 86 | 2-(3-methoxyphenethyl) | 2,4-dichlorophenyl | H |

Preparation 14

The procedure as described for Preparation 1 of Table 1 was repeated using 3,4-dimethylbenzaldehyde, 3-mercaptopropionic acid, and 4-methoxyphenethylamine as starting materials and toluene as the solvent. Yield of desired compound (Entry 2 of Table 2, below): 44% $R_f$ (silica gel): 0.35 (60% hexane; 40% EtOAc): $^1$H NMR (300 MHZ, CDCl$_3$) 7.09 (d, J=8.4 Hz, 3H), 6.93–6.81 (m, 4H), 5.14, (s, 1H), 4.31–4.23 (m, 1H), 3.78 (s, 3H), 2.91–2.68 (m, 6H), 2.60–2.54 (m, 1H), 2.24 (s, 6H); $^{13}$C NMR (75.5 MHz, CDCl$_3$) 169.45, 158.4, 137.1, 136.8, 131.16, 130.0 (two carbons), 129.8, 127.9, 124.0, 114.0 (two carbons), 62.6, 55.2, 50.1, 34.7, 32.9, 21.8, 19.8, 19.3.

Preparation 15

The procedure as described for Preparation 1 of Table 1 was repeated using 3,4-dimethylbenzaldehyde, 3-mercaptopropionic acid, and 2-phenoxylethylamine as starting materials. Yield of desired compound (Entry 12 of Table 2): 49% $R_f$ (silica gel): 0.43 (60% hexane; 40% EtOAc): $^1$H NMR (300 MHz, CDCl$_3$) 7.27 (t, J =7.5 Hz, 2H), 7.14 (d, J=7.8 Hz, 1H), 7.03–6.93 (m, 3H), 6.88 (d, J=7.8 Hz, 2H), 5.83 (s, 1H), 4.39–4.24 (m, 2H), 4.14–4.05 (m, 1H), 3.16–3.07 (m, 1H), 2.88–2.77 (m, 3H), 2.67–2.59 (m, 1H), 2.27 (s, 6H); $^{13}$C NMR (75.5 MHz, CDCl$_3$) 169.9, 158.6, 137.2, 136.8, 129.9, 129.6 (three carbons), 127.9, 124.1, 121.1, 114.6 (two carbons), 66.3, 63.6, 47.3, 34.6, 21.8, 19.8, 19.3.

Preparation 16

The procedure as described for Preparation 1 of Table 1 was repeated using piperonal, 3-mercaptoproprionic acid, and 4-methoxyphenethylamine as starting materials and toulene as the solvent. Yield of desired compound (Entry 18 of Table 2): 15% $R_f$ (silica gel): 0.42 (50% hexane; 50% EtOAc); $^1$H NMR (300 MHz, CDCl$_3$) 7.09 (d, J=8.4 Hz, 2H), 6.82 (d, J=8.4 Hz, 2H), 6.74 (d, J=7.8 Hz, 1H), 6.66 (d, J=1.8 Hz, 1H), 6.59 (dd, J=1.8 and 7.8 Hz, 1H), 5.96 (s, 2H), 5.08 (s, 1H), 4.30–4.21 (m, 1H), 3.78 (s, 3H), 2.89–2.59 (m, 7H); $^{13}$C NMR (75.5 MHz, CDCl$_3$) 169.3, 158.4, 148.3, 147.7, 133.2, 131.1, 129.9 (two carbons), 120.0, 114.0 (two carbons), 107.9, 107.2, 101.5, 62.7, 55.2, 50.0, 34.6, 32.9, 21.9.

Using the principles and techniques of Preparations 14 through 16, and appropriate starting materials, which will be well-understood by those skilled in the art, a variety of other compounds falling within the scope of the present invention can be synthesized. In this regard, metathiazanone compounds (compounds of formula (I) with v=1 and t=0) listed in the following Table 2 can be synthesized.

TABLE 2

| Entry | R¹—X— | R²—Y— | R³ | R⁴ |
|---|---|---|---|---|
| 1 | 2-(4-methylphenethyl) | 4-benzodioxanyl | NHMe | H |
| 2 | 2-(4-methoxyphenethyl) | 3,4-dimethylphenyl | H | H |
| 3 | 2-phenethyl | 4-benzodioxanyl | H | methyl |
| 4 | 2-(4-chlorophenethyl) | phenyl | H | H |
| 5 | 2-(4-ethylphenethyl) | 4-benzodioxanyl | NHSO$_2$Me | H |
| 6 | 2-(2,4-dichlorophenethyl) | 3,4-dimethylphenyl | H | methyl |
| 7 | 3-phenpropyl | 3,4-dimethylphenyl | H | H |

TABLE 2-continued

[Chemical structure: compound with R¹–X–N, R²–Y, ring containing S, R³, R⁴, R⁴, and C=O]

| Entry | R¹—X— | R²—Y— | R³ | R⁴ |
|---|---|---|---|---|
| 8 | 4-methoxybenzyl | 3,4-dimethylphenyl | NHCOPh | H |
| 9 | 4-phenbutyl | 3,4-dimethylphenyl | H | H |
| 10 | 2-(4-bromophenethyl) | 4-benzodioxolanyl | H | H |
| 11 | 2-(3-methoxyphenethyl) | 3,4-dichlorophenyl | H | methyl |
| 12 | 2-phenoxyethyl | 3,4-dimethylphenyl | H | H |
| 13 | 2-(3-methoxyphenethyl) | 3-methoxyphenyl | NHMe | H |
| 14 | 4-methoxybenzyl | 3,4-dimethylphenyl | H | H |
| 15 | 2-(3-methoxyphenethyl) | 2,3-dimethyl-4-methoxyphenyl | H | H |
| 16 | 2-(4-methoxyphenethyl) | 3,4-dichlorophenyl | H | H |
| 17 | 3-phenpropyl | 4-benzodioxolanyl | H | methyl |
| 18 | 2-(4-methoxyphenethyl) | 4-benzodioxolanyl | H | H |
| 19 | 2-(4-methoxyphenethyl) | 3-methyl-4-methoxyphenyl | NHSO₂Ph | H |
| 20 | 2-(4-methoxyphenethyl) | 3-methoxyphenyl | H | methyl |
| 21 | 2-(4-methoxyphenethyl) | 4-ethylphenyl | NHBn | H |
| 22 | 2-(4-chlorophenethyl) | 4-methoxyphenyl | H | H |
| 23 | 2-(4-chlorophenethyl) | 4-dimethylaminophenyl | H | H |
| 24 | 2-phenethyl | 3,4-dimethylphenyl | H | H |
| 25 | 2-phenethyl | 3-methoxyphenyl | H | H |

EXAMPLES

BioAssays

$^{86}$Rb Efflux Assays

Cells stably transfected with cDNA for human Kv1.5 (in pcDNA3 vector) were grown as confluent monolayers in 96 well tissue culture plates in MEM alpha with 10% heat inactivated fetal bovine serum and 400 μg/ml G418. Cells were incubated overnight in growth media containing 1 μCi/ml ; $^{86}$Rb to permit intracellular uptake of the isotope. At the end of the incubation period, the $^{86}$Rb solution is aspirated and the cells washed three times with Earls Balanced Salt Solution (EBSS) which contains (in mM) 132 NaCl, 5.4 KCl, 1.8 CaCl₂, 0.8 mM MgCl₂ 10 mM HEPES and 5 mM glucose. The cells were then preincubated for 10 minutes at room temperature in 100 μl/well of EBSS or EBSS containing test compounds. At the end of this period the wells were aspirated and to each well is then added 100 μl of a modified EBSS solution containing 70 mM KCl (NaCl replaced by KCl) and the compound to be tested. The high KCl concentration is utilized to depolarize the cells to membrane potentials that will activate Kv 1.5 channels. After a 1 minute incubation in 70 mM KCl EBSS plus test compound, the solution is removed and placed into the appropriate well of a 96 well counting plate for analysis. Finally 100 μl of 0.1% sodium dodecyl sulfate in EBSS is added to each well to lyse the cells. The lysate is taken for analysis to determine final cell content of $^{86}$Rb. Samples were counted in a Wallac Microbeta liquid scintillation counter by Cerenkov emission. Efflux is expressed as a percentage of the initial cell content of $^{86}$Rb.

The testing results of selective compounds from Tables 1 and 2 using this assay are reported in Table 3 (flux) as the potency for inhibition of $^{86}$Rb efflux through Kv1.5 potassium channels expressed in CHO cells by compounds of the invention.

Electrophysiological studies

Electrophysiological recordings of potassium currents in Chinese hamster ovary cells stably expressing the gene construct for the Kv1.5 potassium channel subunit were performed using the whole cell configuration of the patch clamp technique (Hamill et al., *Pflugers Archiv* 391:85, 1981). Cell lines expressing Kv1.5 were prepared using standard techniques known to those skilled in the art. Cells were plated on glass coverslips at a density of $2 \times 10^4$ cells/coverslip and used within 24–48 hours. Solutions used for electrophysiological recordings were as follows. Extracellular bathing solutions contained (in mM) 132 NaCl, 5.4 KCl, 1.8 CaCl₂, 0.8 MgCl₂, 10 HEPES, 5 glucose at pH 7.3. Electrode pipette solutions for measuring Kv1.5 contain (in mM) 100 KF, 40 KCl, 5 NaCl, 2 MgCl₂, 5 mM EGTA, 10 mM HEPES and 5 glucose at pH 7.4, 295 mOsm. The coverslips were placed in a small chamber (volume~200 μl) on the mechanical stage of an inverted microscope and perfused (2 ml/min) with extracellular recording solution. Drug application is achieved via a series of narrow-bore glass capillary tubes (inner diameter~100 μm) positioned approximately 200 μm from the cell.

The testing results of selective compounds from Tables 1 and 2 using this assay are reported in Table 3 (EP) as the potency for inhibition of Kv1.5 potassium currents by compounds of the invention.

TABLE 3

| Entry | Table | IC₅₀ (μM) (EP) | IC₅₀ (μM) (flux) |
|---|---|---|---|
| 1 | 1 | 0.6 | 3.9 |
| 5 | 1 | 6.0 | 29.6 |
| 8 | 1 | 1.2 | 9.9 |
| 23 | 1 | ND | 14.5 |
| 36 | 1 | 4.7 | 30.0 |
| 45 | 1 | 0.6 | ND |
| 52 | 1 | 0.2 | 0.9 |
| 60 | 1 | 0.3 | 6.9 |
| 67 | 1 | 0.7 | 1.3 |
| 77 | 1 | 1.6 | 10.5 |
| 82 | 1 | ND | 4.7 |
| 2 | 2 | 0.3 | 1.5 |
| 18 | 2 | 1.0 | 1.5 |

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications based on the above disclosure for making and using the compounds of the invention.

In the forgoing specification, the following abbreviations are used:

| Designation | Reagent or Fragment |
| --- | --- |
| UV | ultra-violet |
| KMnO$_4$ | potassium permanganate |
| KOH | potassium hydroxide |
| NMR | nuclear magnetic resonance |
| Hz | hertz |
| MHz | megahertz |
| EtOAc | ethyl acetate |
| NaHCO$_3$ | sodium bicarbonate |
| HCl | hydrochloric acid |
| NaCl | sodium chloride |
| Na$_2$SO$_4$ | sodium sulfate |
| R$_f$ | retention factor |
| CDCl$_3$ | chloroform-d |
| NEt$_3$ | triethylamine |
| Bn | benzyl |
| Me | methyl |
| Ph | phenyl |

We claim:

1. A method for treating a disease, condition, or disorder which responds to the inhibition of potassium channel function by administering to a patient in need thereof, a pharmaceutically effective amount of a compound having the following formula, or a pharmaceutically acceptable salt, ester, amide, complex, chelate, hydrate, stereoisomer, crystalline or amorphous form, metabolite, metabolic precursor or prodrug thereof:

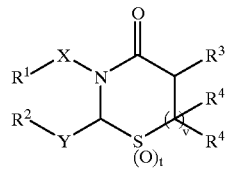

(I)

wherein, v is 0 or 1;

t is 0, 1, or 2;

X, in an orientation R$^1$—X—, is selected from
—(CR$^4_2$)$_p$—; —(CR$^4_2$)$_m$O(CR$^4_2$)$_m$CH=CH(CR$^4_2$)$_s$—; —(CR$^4_2$)$_m$CH≡CH(CR$^4_2$)$_s$—; —(CR$^4_2$)$_m$—A—(CR$^4_2$)$_m$—;

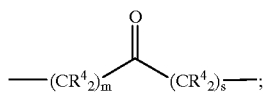

—(CR$^4_2$)$_m$—NR$^4$—(CR$^4_2$)$_n$—;

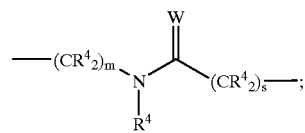

and

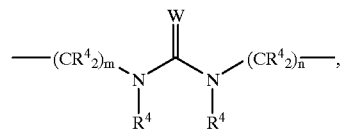

where p is an integer of 0 to 5, n is an integer of 2 to 4, m is an integer of 0 to 4 and s is an integer of 1 to 4; A is selected from an optionally substituted 3 to 7 membered carbocyclic ring and an optionally substituted 5 to 7 membered heterocyclic ring; each R$^4$ is independently selected from H, a lower alkyl, an aryl and a heteroaryl; W is selected from 0 and NR$^5$ where R$^5$ is selected from H lower alkyl, aryl, C≡N and NHR$^4$;

R$^1$ is selected from H, an optionally substituted aryl and an optionally substituted heteroaryl;

Y, in an orientation R$^2$—Y—, is selected from —(CR$^4_2$)$_q$—; —(CR$^4_2$)$_m$O(CR$^4_2$)$_n$—; —(CR$^4_2$)$_m$CH=CH(CR$^4_2$)$_m$—; —(CR$^4_2$)$_m$CH≡CH(CR$^4_2$)$_m$—; —(CR$^4_2$)$_m$—A—(CR$^4_2$)$_m$— and a cycloalkyl, where q is an integer of 0 to 4 and m and n are as defined above;

R$^2$ is selected from H, an optionally substituted aryl and an optionally substituted heteroaryl; and R$^3$ is selected from H, optionally substituted lower allyl, optionally substituted aryl, optionally substituted heteroaryl and —NR$^6$R$^7$, where R$^6$ is selected from H and optionally substituted lower alkyl; R$^7$ is H, optionally substituted lower alkyl, optionally substituted aryl, —(SO$_2$)R$^8$, —COR$^8$ and —C(O)NH—R$^4$, R$^8$ is selected from optionally substituted lower alkyl, optionally substituted aryl and optionally substituted heteroaryl or R$^6$ and R$^7$ together with the nitrogen to which they are attached form a heteroaryl.

2. The method of claim 1 wherein t is 0.

3. A method for treating a disease, condition, or disorder which responds to the inhibition of potassium channel function by administering to a patient in need thereof, a pharmaceutically effective amount of a compound having the following formula or a pharmaceutically acceptable salt, ester, amide, complex, chelate, hydrate, stereoisomer, crystalline or amorphous form, metabolite, metabolic precursor or prodrug thereof:

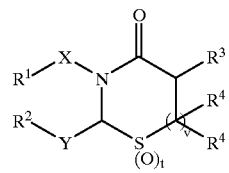

(I)

wherein, v is 0;

t is 0, 1, or 2;

X, in an orientation $R^1$—X—, is selected from —$(CR^4_2)_p$—; —$(CR^4_2)_mO(CR^4_2)_n$—; —$(CR^4_2)_m$CH=CH$(CR^4_2)_s$—; —$(CR^4_2)_m$CH≡CH$(CR^4_2)_s$—; and —$(CR^4_2)_m$—A—$(CR^4_2)_m$—; where p is an integer of 0 to 5, n is an integer of 2 to 4, m is an integer of 0 to 4 and s is an integer of 1 to 4; A is an optionally substituted 3 to 7 membered carbocyclic ring; each $R^4$ is independently selected from H, a lower alkyl, an aryl and a heteroaryl;

$R^1$ is selected from an optionally substituted aryl and an optionally substituted heteroaryl;

Y, in an orientation $R^2$—Y—, is selected from —$(CR^4_2)_q$—; —$(CR^4_2)_mO(CR^4_2)_n$—; —$(CR^4_2)_m$CH=CH$(CR^4_2)_m$—; —$(CR^4_2)_m$CH≡CH$(CR^4_2)_m$—; —$(CR^4_2)_m$—A—$(CR^4_2)_m$— and a cycloalkyl, where q is an integer of 0 to 4 and m and n are as defined above;

$R^2$ is selected from H, an optionally substituted aryl and an optionally substituted heteroaryl; and $R^3$ is selected from H, optionally substituted lower alkyl, optionally substituted aryl, optionally substituted heteroaryl and —$NR^6R^7$, where $R^6$ is selected from H and optionally substituted lower alkyl; $R^7$ is H, optionally substituted lower alkyl, optionally substituted aryl, —$(SO_2)R^8$, —$COR^8$ and —$C(O)NH$—$R^4$, $R^8$ is selected from optionally substituted lower alkyl, optionally substituted aryl and optionally substituted heteroaryl or $R^6$ and $R^7$ together with the nitrogen to which they are attached form a heteroaryl.

4. The method of claim 3 wherein v is 0 and t is 0.

5. A method for treating a disease, condition, or disorder which responds to the inhibition of potassium channel function by administering to a patient in need thereof, a pharmaceutically effective amount of a compound having the following formula or a pharmaceutically acceptable salt, ester, amide, complex, chelate, hydrate, stereoisomer, crystalline or amorphous form, metabolite, metabolic precursor or prodrug thereof;

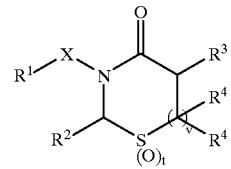

wherein, v is 0;

t is 0, 1, or 2;

X, in an orientation $R^1$—X—, is selected from —$(CR^4_2)_p$—; —$(CR^4_2)_m$CH=CH$(CR^4_2)_s$—; —$(CR^4_2)_m$CH≡CH$(CR^4_2)_s$—; and —$(CR^4_2)_m$—A—$(CR^4_2)_m$—; where p is an integer of 0 to 5, n is an integer of 2 to 4, m is an integer of 0 to 4 and s is an integer of 1 to 3; A is an optionally substituted 3 to 7 membered carbocyclic ring; each $R^4$ is independently selected from H, a lower alkyl, an aryl and a heteroaryl;

$R^1$ is selected from an optionally substituted aryl and an optionally substituted heteroaryl;

$R^2$ is an optionally substituted phenyl; and $R^3$ is selected from H, optionally substituted lower alkyl, optionally substituted aryl, optionally substituted heteroaryl and —$NR^6R^7$, where $R^6$ is selected from H and optionally substituted lower alkyl; $R^7$ is H, optionally substituted lower alkyl, optionally substituted aryl, —$(SO_2)R^8$, —$COR^8$ and —$C(O)NH$—$R^4$, $R^8$ is selected from optionally substituted lower alkyl, optionally substituted aryl and optionally substituted heteroaryl or $R^6$ and $R^7$ together with the nitrogen to which they are attached form a heteroaryl.

6. The method of claim 5 wherein t is 0.

7. The method of claim 1 wherein said disease, condition or disorder is cardiac arrhythmia.

* * * * *

UNITED STATES PATENT AND TRADEMARK OFFICE
CERTIFICATE OF CORRECTION

PATENT NO.   : 6,174,908 B1
DATED         : January 16, 2001
INVENTOR(S) : Michael F. Gross et al.

It is certified that error appears in the above-identified patent and that said Letters Patent is hereby corrected as shown below:

Title page,
Filing date, "May 1, 1999" has been deleted and in its place -- May 10, 1999 -- has been inserted.

Column 27, claim 1,
Line 55, "v is 0 or 1;" has been deleted and in its place -- v is 0; -- has been inserted.

Signed and Sealed this

First Day of January, 2002

Attest:

Attesting Officer

JAMES E. ROGAN
Director of the United States Patent and Trademark Office